United States Patent
Chong et al.

(10) Patent No.: US 9,955,687 B2
(45) Date of Patent: May 1, 2018

(54) POLYMERIC FILM SURFACE (71) Applicants: Agency for Science, Technology and Research, Singapore (SG); Ngee Ann Polytechnic, Singapore (SG); Temasek Polytechnic, Singapore (SG); Singapore Polytechnic, Singapore (SG)

(72) Inventors: Karen Siew Ling Chong, Singapore (SG); Yeong Yuh Lee, Singapore (SG); Seok Hong Goh, Singapore (SG); Kevin Beng Chin Khaw, Singapore (SG); Ryan Chaw, Singapore (SG); Hong Yee Low, Singapore (SG); Adrian Yeo, Singapore (SG); Weng Keong Choy, Singapore (SG); Han Liat Loh, Singapore (SG)

(73) Assignees: AGENCY FOR SCIENCE, TECHNOLOGY AND RESEARCH, Singapore (SG); TEMASEK POLYTECHNIC, Singapore (SG); NGEE ANN POLYTECHNIC, Singapore (SG); SINGAPORE POLYTECHNIC, Singapore (SG)

(*) Notice: Subject to any disclaimer, the term of this patent is extended or adjusted under 35 U.S.C. 154(b) by 84 days.

(21) Appl. No.: 14/402,054

(22) PCT Filed: May 20, 2013

(86) PCT No.: PCT/SG2013/000204
§ 371 (c)(1),
(2) Date: Nov. 18, 2014

(87) PCT Pub. No.: WO2013/172794
PCT Pub. Date: Nov. 21, 2013

(65) Prior Publication Data
US 2015/0104622 A1    Apr. 16, 2015

(30) Foreign Application Priority Data
May 18, 2012 (SG) ............... 201203692-7

(51) Int. Cl.
B32B 3/10 (2006.01)
A01N 25/34 (2006.01)
(Continued)

(52) U.S. Cl.
CPC ........... *A01N 25/34* (2013.01); *B63B 59/045* (2013.01); *C09D 5/1681* (2013.01); *Y10T 428/24802* (2015.01)

(58) Field of Classification Search
None
See application file for complete search history.

(56) References Cited

U.S. PATENT DOCUMENTS

2007/0227428 A1* 10/2007 Brennan ............. B08B 17/06
114/67 R

FOREIGN PATENT DOCUMENTS

JP   H0717476    1/1995
JP   2001114185  4/2001
(Continued)

OTHER PUBLICATIONS

"International Application No. PCT/SG2013/000204, International Preliminary Report on Patentability dated Apr. 8, 2014", (dated Apr. 8, 2014), 18 pgs.
(Continued)

*Primary Examiner* — Christopher Polley
(74) *Attorney, Agent, or Firm* — Choate, Hall & Stewart LLP (57) ABSTRACT

A surface on a polymeric film having an array of patterned structures, wherein the array of patterned structures influ-
(Continued)

ences fluid flow of the surface and causes reduced attachment of a biological material.

21 Claims, 7 Drawing Sheets (51) Int. Cl.
*B63B 59/04* (2006.01)
*C09D 5/16* (2006.01)

(56) References Cited

FOREIGN PATENT DOCUMENTS

| WO | WO-2002/062568 | 8/2002 |
| WO | WO-2008/070625 | 6/2008 |
| WO | WO-2010/056824 | 5/2010 |
| WO | WO-2013/172794 | 11/2013 |

OTHER PUBLICATIONS

"International Application No. PCT/SG2013/000204, International Search Report and Written Opinion dated Aug. 8, 2013", (dated Aug. 8, 2013), 12 pgs.

\* cited by examiner

POLYMERIC FILM SURFACE

PRIORITY CLAIM TO RELATED APPLICATIONS

This application is a U.S. national stage application filed under 35 U.S.C. § 371 from International Application Serial No. PCT/SG2013/000204, which was filed May 20, 2013, and published as WO 2013/172794 on Nov. 21, 2013, and which claims priority to Singapore Application No. 201203692-7, filed May 18, 2012, which applications and publication are incorporated by reference as if reproduced herein and made a part hereof in their entirety, and the benefit of priority of each of which is claimed herein.

TECHNICAL FIELD

The present invention generally relates to surface on a polymeric film having an array of patterned surfaces. The present invention also relates to a method of reducing attachment of a biological material on a surface of a polymeric film.

BACKGROUND

Fouling is the undesired accumulation of organic and inorganic matter of biological origin on surface. Fouling is an issue which persistently occurs across several industries such medical, food manufacturing, marine and even water filtration. Such matter may include bacteria or proteins which tend to adhere stubbornly onto flat or smooth surfaces.

Conventional strategies to tackle fouling issues on the surface of an article include pre-sterilization of the article itself or incorporation of the use of biocidal agents or anti-adhesive coatings. However, such means remain ineffective or may result in further problems down the track. Pre-sterilization strategies may be used to eliminate contaminants effectively prior to use but such methods may not be applicable for all articles. There is also a residual risk that contamination may occur after the pre-sterilized article is removed from its packaging. Hence, the effectiveness of the fouling resistance of such pre-sterilized article is short-lived. In addition, the use of biocidal agents such as silver, triclosan or antibiotics in the material or on material surfaces may provide passive deterrence to fouling, but their use may be harmful towards the environment and human health. Likewise, the effective of these biocidal agents do not last for long.

In another instance, a requirement of anti-adhesive coatings on long-standing infrastructure and vessels is that these coatings should be able to retain its resistance to fouling so as to provide for a longer period of protection. Although the application of anti-adhesive coatings such as polyethylene glycol (PEG) may be used to reduce the adhesion of biological materials such as proteins and micro-organisms, these coatings are not durable and are unable to withstand the wear- and tear associated with certain applications.

Therefore, there is a need to provide an article with the means to resist fouling.

There is also a need to provide an article with the means to reduce attachment or retention of a biological material.

SUMMARY

According to a first aspect, there is provided a surface on a polymeric film having an array of patterned structures, wherein the array of patterned structures influences fluid flow of the surface and causes reduced attachment of a biological material.

Advantageously, the array of patterned structures may influence the fluid flow on the surface during washing or rinsing of the polymeric film to facilitate the removal of the biological material from the surface. This may aid in reducing the attachment of the biological material on the surface.

The array of patterned structures may induce turbulent fluid flow on the surface so as to reduce the attachment of the biological material on the surface.

The patterned structures may be spaced apart or may be dimensioned such that the spacing or dimension is greater than the size of the biological material.

The reduction in the attachment of the biological material on the surface may be a physical means that is attributable to the patterned structures. The reduction in the attachment of the biological material on the surface may optionally exclude chemical means, for example, applying an anti-adhesive coating or treating the surface with a chemical agent.

The reduction in the attachment of the biological material on the surface may not rely on the contact area of the surface or on the mechanical properties of the surface (or polymeric film) such as tensile forces, material stiffness or elasticity. In addition, the reduction in the attachment of the biological material on the surface may not be dependent on the wetting property (such as hydrophobicity) of the surface.

As the patterned structures are part of the surface, as compared to a chemical coating on the surface, the patterned structures may be more durable and longer lasting as compared to conventional surfaces. In addition, as the use of toxic chemicals to alter the surface properties is not required, the patterned structures may be a non-toxic way to modify the surface in order to reduce attachment of the biological material.

According to a second aspect, there is provided a method of reducing attachment of a biological material on a surface of a polymeric film comprising the step of providing an array of patterned structures on the surface, the array of patterned structures being selected to influence fluid flow of the surface to thereby cause reduced attachment of the biological material.

Advantageously, the method may optionally exclude the step of chemically modifying the surface.

DEFINITIONS

The following words and terms used herein shall have the meaning indicated:

The terms "microscale", "micro-sized" or "micro-range" is to be interpreted broadly to include any dimensions that are in the range of about 1 (μm) to about 100 μm. The term "microstructures" as used herein, refers to patterned structures comprising "microscale" features.

The terms "nanoscale", "nano-sized" or "nano-range" is to be interpreted broadly to include any dimensions that are below about 1 μm. The term "nanostructures" as used herein, are patterned structures comprising "nanoscale" or "submicron" features.

The terms "pillar" or "pillar-shaped" is to be interpreted broadly to include any substantially upright longitudinal body where the length is much greater than the width and where the width dimension is relatively constant throughout the length dimension.

The term "groove" is to be interpreted broadly to include any depression that extends into the body of the polymeric film from the surface and where the longitudinal axis of the groove is substantially parallel to a side of the surface. The groove may have an anisotropic cross-sectional shape such as a "V-shape" or a "U-shape".

The term "array" generally refers to multiple numbers of patterned structures distributed within an area and spaced apart, unless otherwise indicated. Structures within an array may not necessarily have the same orientation, unless otherwise indicated.

The term "ordered array" generally refers to the placement of the patterned structures in a specified or predetermined pattern where the patterned structures have distinct spatial relationships to one another. Hence, the term "ordered array" generally refers to structures distributed within an area with distinct, specified or predetermined spatial relationships to one another. For example, the spatial relationships within an ordered array may be such that the structures are spaced apart from one another by generally equal distances. Other ordered arrays may use varying, but specified or predetermined, spacings.

The term "glass transition temperature" (Tg) is to be interpreted to include any temperature of a polymer at which the polymer lies between the rubbery and glass states. This means that above the Tg, the polymer becomes rubbery and can undergo elastic or plastic deformation without fracture. Above this temperature, such polymers can be induced to flow under pressure. When the temperature of the polymer falls below the Tg, generally, the polymer will become inflexible and brittle such that it will break when a stress is applied to the polymer. It should be noted that the Tg is not a sharp transition temperature but a gradual transition and is subject to some variation depending on the experimental conditions (e.g., film thickness, tacticity of the polymer, etc.). The actual Tg of a polymer film will vary as a function of film thickness. The Tg will be defined herein as being the bulk glass-transition temperature of the polymer substrate.

The term "biological material" is to be interpreted broadly to refer to any cells, organisms or component that has a biological origin. Hence, the biological material may include viruses, eukaryotic, organisms, bacteria, fungi or proteins.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a surface on a polymeric film having an array of patterned structures will now be disclosed.

The array of patterned structures on the surface may influence fluid flow of the surface and may cause reduced attachment of a biological material.

The patterned structures of the surface may promote turbulent fluid flow on the surface during washing or rinsing of the surface, the turbulent fluid flow serving to reduce the attachment of the biological material to the surface. The turbulent fluid flow may be created as a result of the topographies of the patterned structures which may perturb flow over a surface.

The array of patterned structures may comprise of protrusions and depressions. The protrusions may be pillars or pillar-shaped structures. The depressions may be grooves.

The structures may be micro-sized or nano-sized. The pillars or pillar-shaped structures may be micron-sized or nano-sized. Each pillar in the array may have a width or diameter in the range selected from about 10 nm to about 50 μm, about 25 nm to about 50 μm, about 100 nm to about 50 μm, about 500 nm to about 50 μm, about 2 μm to about 50 μm, about 10 μm to about 50 μm, about 10 nm to about 25 nm, about 10 nm to about 100 nm, about 10 nm to about 500 nm, about 10 nm to about 2 μm, or about 10 nm to about 10 μm. The diameter of each pillar may be selected from 25 nm, 100 nm, 500 nm, 2 μm or 10 μm.

The pillars may be spaced apart from each other according to a predetermined spacing. This spacing may be determined as the distance between adjacent pillars, based on the edge to the nearest edge of the next pillar. The spacing between a pair of pillars may be the same as the spacing between another pair of pillars or the spacing between a pair of pillars may be different from the spacing between another pair of pillars. The spacing may be typically larger than the size of the biological material such that the biological material can be deemed as residing in the space between a plurality of pillars. The spacing may be in the micron-scale or in the nano-scale. The spacing may be equal to the width or diameter of the pillars or may be different from the width or diameter of the pillars. The spacing may be in the range selected from about 10 nm to about 100 μm, about 10 nm to about 25 nm, about 10 nm to about 100 nm, about 10 nm to about 500 nm, about 10 nm to about 2 μm, about 10 nm to about 10 μm, about 10 nm to about 20 μm, about 10 nm to about 50 μm, about 2 μm to about 100 μm, about 2 μm to about 6 μm, about 2 μm to about 20 μm, about 2 μm to about 50 μm, about 6 μm to about 100 μm, about 20 μm to about 100 μm or about 50 μm to about 100 μm. The spacing may be selected from 25 nm, 100 nm, 500 nm, 2 μm, 6 μm, 10 μm, 20 μm or 50 μm.

The patterned structures may be pillars having a diameter of 10 µm which are spaced apart at a spacing of 6 µm, 20 µm or 50 µm. The patterned structures may be pillars having a diameter of 25 nm, 100 nm, 500 nm, 2 µm or 10 µm, which are spaced apart at a spacing that is equal to the diameter of the pillars.

The grooves may have a dimension that is micron-sized or nano-sized. The dimension may be in the range selected from about 100 nm to about 5 µm, about 500 nm to about 5 µm, about 2 µm to about 5 µm, about 100 nm to about 500 nm or about 100 nm to about 2 µm. The dimension may be deemed as the width of the groove which is the distance between the tips of the groove.

The grooves may have cross-sectional shape which may be viewed as a V shape configuration or a U shape configuration. The V-shape grooves may have a width selected from 100 nm, 500 nm, 2 µm or 10 µm wherein the width is measured from the top of the groove. The U-shape grooves may have a width selected from 500 nm, 2 µm or 10 µm, wherein the width is measured from the top of the groove.

The grooves may be spaced apart from each other. The spacing may be selected from 100 nm, 500 nm, 2 µm or 10 µm.

The continuous grooves may aid, in channeling the fluid flow along a certain direction. By determining the direction of the fluid flow, the polymeric film may be washed and rinsed in this direction in order to allow the washing medium to be removed easily from the polymeric film by following the orientation of the grooves. Hence, the washing medium and the directional effects may also aid to wash away any biological material that may be attached to the surface of the polymeric film.

The biological material is not particularly limited and can include any biological material in which its attachment to a particular surface is to be reduced in order to minimize contamination or inhibition of biological processes, for example. Exemplary biological material may be selected from the group consisting of proteins, eukaryotic organisms, bacteria, viruses or fungi.

Where the biological material is a protein, exemplary protein may include peptides, enzymes, antibodies or antigens.

Where the biological material is a bacteria, an exemplary bacteria may be selected from gram negative bacteria, gram positive bacteria or marine bacteria. Exemplary bacteria may be selected from *E. coli* (such as *E. coli* ATCC 25922), *S. epidermidis* (such as *S. epidermidis* ATCC 12228), *P. Tunicata* (such as *P. Tunicata* D2), *staphylococcus aureus, streptococcus pyogenes, salmonella* spp, *shigella* spp, *Neisseria, pseudomonas aeruginosa, Yersinia, campylobacter, legionella, aeromonas, mycobacterium avium, helicobacter pylori*, etc.

Where the biological material is an eukaryotic organism, an exemplary eukaryotic organism may be a protozoa such as *Giardia lamblia, Cryptosporidium parvum, Cyclospora, Isospora*, etc.

Where the biological material is a virus, exemplary virus may be selected from *Cryptosporidium*, adenovirus, herpesvirus, poxvirus, parvovirus, reovirus, picornavirus, togavirus, oethomyxovirus, rhabdovirus, retrovirus, hepadnavirus, etc.

Where the biological material is a fungi, an exemplary fungi may be mold or yeast.

The patterned structures on the surface may be formed by lithography (such as photolithography, electron beam lithography or nanoimprinting lithography) or etching. The patterned structures on the surface may be formed by nanoimprinting lithography. Briefly, a mold having the inverse of the structures to be imprinted is applied to a thermoplastic polymer at a temperature above the glass transition temperature of the thermoplastic polymer. The applying temperature may be in the range of about 60° C. to about 250° C. or about 120° C. to about 200° C. At this temperature, the thermoplastic polymer may become semi-molten or fully molten such that it is able to flow into the crevices of the mold. The polymer and mold are then cooled in order to harden the polymer and the mold is removed from the polymer. The resultant polymer is one which has patterned structures on the surface.

There is also provided a method of reducing attachment, of a biological material on a surface of a polymeric film. The method comprises the step of providing an array of patterned structures on the surface, the array of patterned structures being selected to influence fluid flow of the surface to thereby cause reduced attachment of the biological material.

The method may comprise the step of selecting the array of patterned structures to promote turbulent fluid flow on the surface. The method may comprise the step of selecting the array of patterned structures to promote fluid flow along a desired direction (or also termed as directional flow) on the surface. The array of patterned structures may control the flow of direction of the fluid along a desired direction. In general, in order to have turbulent flow, isolated structures like pillars can be used, while anisotropic structures such as the groves (of the V shaped or U shaped) can result in directional flow. The array of patterned structures may include both isolated pillars and anisotropic structures on the same surface so as to have both the turbulent flow and directional flow.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Figure 1:
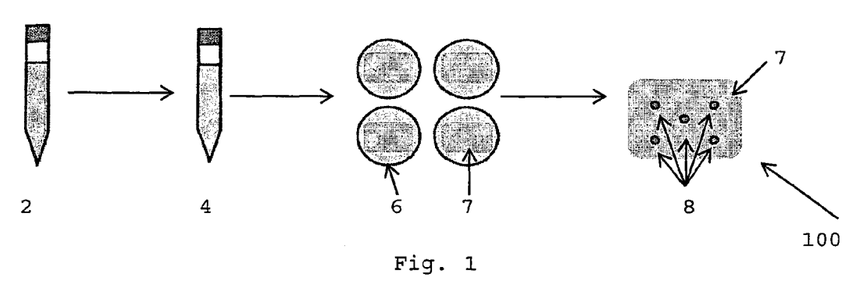
FIG. 1 is a schematic diagram showing the protocol used for testing the extent of microorganism adhesion on test patterned substrates.

Referring to FIG. 1, there is shown a schematic diagram of a protocol 100 used to test the extent of microorganism adhesion on test patterned substrates. Firstly, a shake culture 2 of a test microorganism was cultivated for a period of time in sterile culture medium. The shake culture 2 is then diluted to form a working microorganism culture 4. Following which, a certain amount of the working microorganism culture 4 is dispensed onto wells 6 containing the test patterned substrates 7. The test patterned substrates 7 are then stained with a fluorescence agent and imaged with a suitable microscope at five different spots 8 to determine the amount of adhered microorganism on the test patterned substrates 7.

Figure 2:
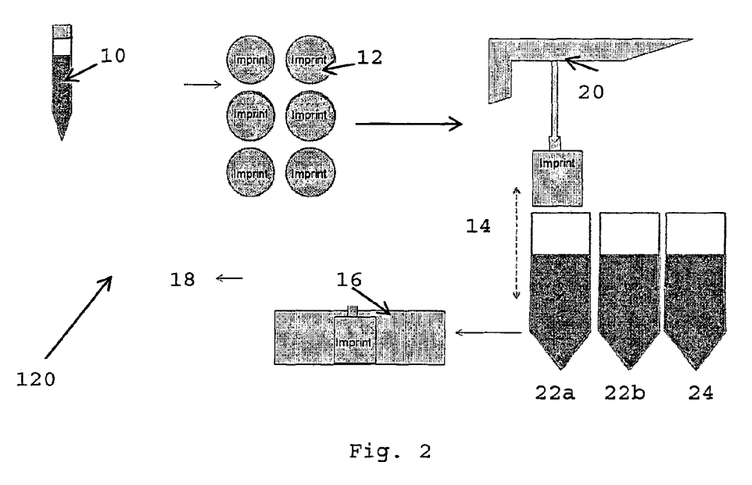
FIG. 2 is a schematic diagram showing the dip test protocol used to test the extent of microorganism adhesion on test patterned substrates after repeated washing and rinsing steps.

Referring to FIG. 2, there is shown a schematic diagram showing the dip test protocol 120 used to test the extent of microorganism adhesion on test patterned substrates after repeated washing and rinsing steps. Firstly, a shake culture 10 of a test microorganism was cultivated for a period of time in sterile culture medium until the mid-log phase. The test patterned substrates (or imprints) 12 are loaded into 6-well plate and incubated with the shake culture 10. The test patterned substrate 12 is then loaded onto a dipper 20. The test patterned substrate 12 is then dipped and rinsed successively in a number of washing media (22a, 22b, 24) following the direction of the arrow 14. During each dipping and rinsing, the horizontal and vertical directions of the test patterned substrate 12 are controlled in order to determine the directional effect of the patterned structures present on the test patterned substrate 12. After dipping and rinsing, the retained microorganism on the surface of the test patterned substrate 12 were mounted on a slide 16 and the concentration of microorganism is then determined by averaging the cell counts of five fluorescent images using a Cell Profiler 18.

Figure 7:
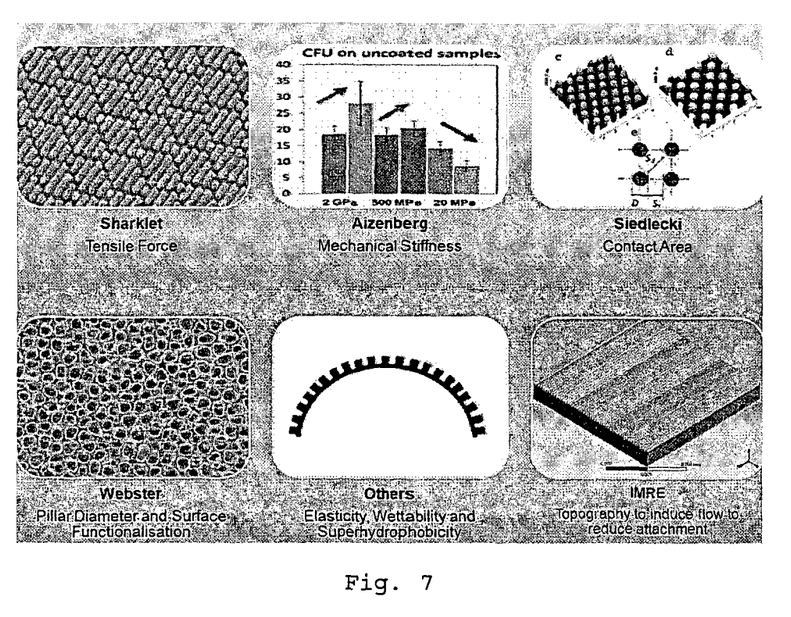
FIG. 7 is a diagram showing the comparison between conventional mechanisms used to reduce biological material attachment and the disclosed polymeric film (shown as "IMRE" in FIG. 7).

FIG. 7 shows the mechanism of the disclosed polymeric film (labeled as "IMRE") which uses surface topography to reduce attachment of a biological material, such as bacteria. This is in comparison to conventional mechanisms of tensile force ("sharklet"), mechanical stiffness ("Aizenberg"), contact angle ("Siedlecki"), surface functionalization ("webster") and wetting property effects ("others"). Hence, the conventional mechanisms are based on designs that would change the mechanical properties such as tensile strength and elasticity, or on the use of surface topography to change the wettability of the substrate and hence influence bacterial attachment. However, none of the topographies presented in the conventional mechanisms are based on topographical designs that reduce the attachment of the biological material by influencing and manipulating the fluid flow on the surface. Based on the V groove structures (having a width of 2 μm and a spacing of less than 200 nm) and on E. coli as the test bacteria, up to 74.16% in reduction as compared to a control (a blank, unpatterned substrate) and up to 166.39% reduction as compared to commercial Sharklet™ can be achieved in the disclosed polymeric film.

EXAMPLES

Non-limiting examples of the invention will be further described in greater detail by reference to specific Examples, which should not be construed as in any way limiting the scope of the invention.

Example 1

The protocol 100 of FIG. 1 was used in this example to study the attachment of micro-organism on the test patterned substrate 7. Firstly, a shake culture 2 of a test microorganism such as E. coli ATCC 25922 (a gram negative bacteria, obtained from ATCC of Virginia of the United States of America) was cultivated for 18 hours in sterile culture medium of tryptic soy broth (from BD Diagnostics, obtained from Biomed Diagnostics of Singapore) at a temperature of 35° C.±2° C. E. coli ATCC 25922 is a rod-shaped bacterium with diameter of about 0.5 μm and a length of about 1 to 2 μm. The shake culture 2 was then diluted with sterile tryptic soy broth to form a working microorganism culture 4 such as working bacterial culture 4 with a concentration of 1.0 to $2.0 \times 10^8$ CFU/ml. Following which, 3 ml of the working bacterial culture 4 (~$1-2 \times 10^8$ CFU/ml) was dispensed onto wells 6 containing the test patterned substrates 7. The test patterned substrates 7 were imprinted with various nano and micron sized structures. The test patterned substrates 7 were incubated at 125 rpm for 1 hour at a temperature of 35° C. After incubation, the test patterned substrates 7 were rinsed in saline and stained with a fluorescence agent such as BacLight viability stains for 15 minutes. After staining, the test patterned substrates 7 were further rinsed with de-ionized water and mounted for fluorescence microscopy at five different spots 8 to determine the amount of adhered bacteria on the test patterned substrates 7. Under the fluorescence microscope, live bacteria are detected as green while dead bacteria are detected as red due to the different penetrative ability of the dyes in the viability stains. From the microscopy images, the number of pixels occupied by the bacteria were measured and the mean number of bacteria adhered on the surface after the above protocol was estimated, thus quantifying the number of bacteria adhered or retained on the surface of the test patterned substrates 7 after a series of rinsing steps.

The same protocol was carried out for a gram positive bacteria such as S. epidermidis ATCC 12228 (obtained from ATCC of Virginia of the United States of America) and a marine bacteria such as P. Tunicata D2 (obtained from culture collection of the University of Gothenburg of Sweden). S. epidermidis ATCC 12228 is a spherical-shaped bacterium with a diameter of about 0.5 to 1.5 μm, while P. Tunicata D2 is a rod-shaped bacterium with diameter of about 0.8 μm and length of about 2 to 3 μm. The results of this example are shown in Table 1 (for E. coli ATCC 25922), Table 2 (for S. epidermidis ATCC 12228) and Table 3 (for P. Tunicata D2) below. The percentage reductions are calculated as follows: each particular patterned structure is tested on 3 different days and for each particular day, 3 samples for each patterned structure were tested. The mean for each patterned structure was then calculated and the reductions compared to the controls were taken.

Table 1: Table Showing the % Reduction of *E. coli* ATCC 25922 for Pillars with Different Dimensions (with Spacing Equal to the Dimension), Pillars with Varying Spacing, V Grooves and U Grooves

TABLE 1-1

Figure 3A:
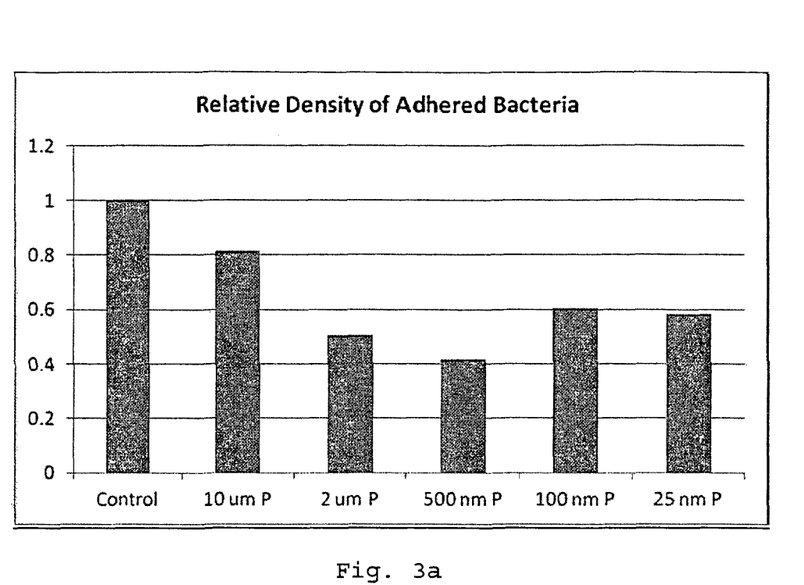
FIG. 3a is a bar graph showing the reduced mean number of adhered *E. coli* ATCC 25922 per mm$^2$ for pillars with different dimensions.

(see also FIG. 3a)

| Patterns | % reduction |
| --- | --- |
| 10 um diameter pillars | 18.53 |
| 2 um diameter pillars | 49.58 |
| 500 nm diameter pillars | 58.24 |
| 100 nm diameter pillars | 39.45 |
| 25 nm diameter pillars | 41.92 |

TABLE 1-2

Figure 3B:
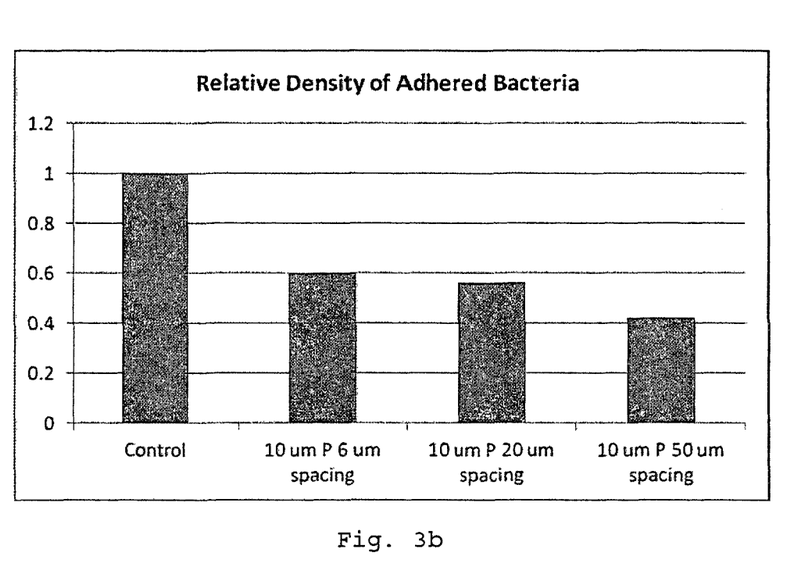
FIG. 3b is a bar graph showing the reduced mean number of adhered *E. coli* ATCC 25922 per, mm$^2$ for pillars with varying spacings.

(see also FIG. 3b)

| Patterns | % reduction |
| --- | --- |
| 10 um diameter with 6 um spacing | 39.99 |
| 10 um diameter with 20 um spacing | 43.75 |
| 10 um diameter with 50 um spacing | 57.93 |

TABLE 1-3

Figure 3C:
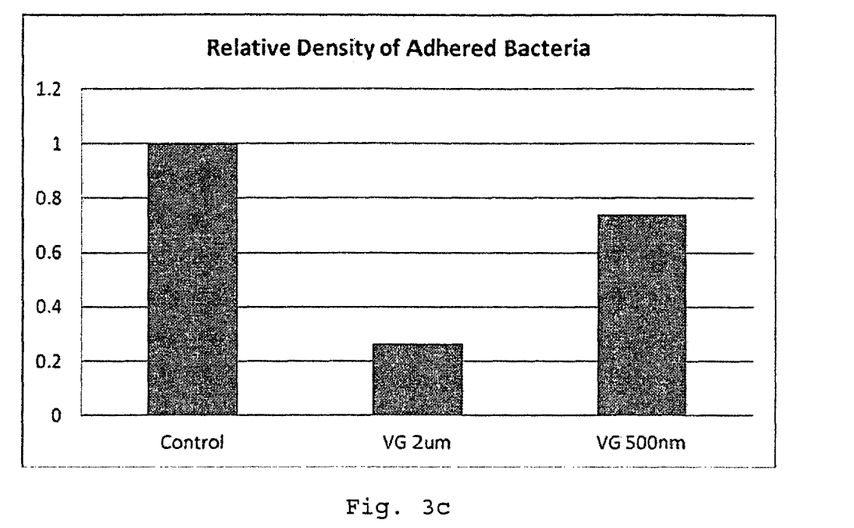
FIG. 3c is a bar graph showing the reduced mean number of adhered *E. coli* ATCC 25922 per mm$^2$ for V grooves of different widths.

(see also FIG. 3c)

| Patterns | % reduction |
| --- | --- |
| V grooves 2 um | 73.5 |
| V grooves 500 nm | 26.07 |

TABLE 1-4

Figure 3D:
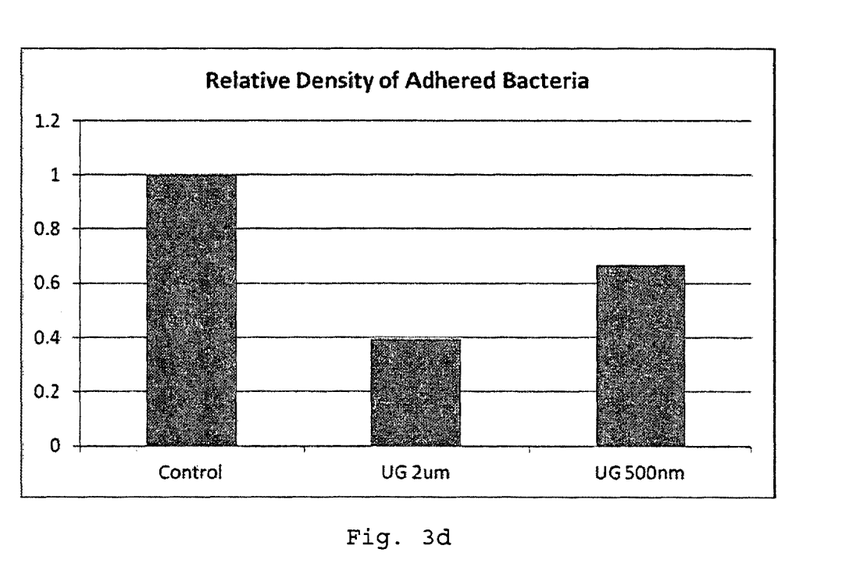
FIG. 3d is a bar graph showing the reduced mean number of adhered *E. coli* ATCC 25922 per mm$^2$ for U grooves of different widths.

(see also FIG. 3d)

| Patterns | % reduction |
| --- | --- |
| U grooves 2 um | 60.45 |
| U grooves 500 nm | 33.14 |

In Table 1-1, the spacings between the pillars were equal to the diameters of the pillars. Table 1-1 investigates the changes in diameter of the pillars while Table 1-2 investigates the effect of spacings (between the pillars) on the % bacterial reduction. The results from Table 1-1 and those of Table 1-2 were carried out in independent sets. As there is a correlation between the diameter of the pillars and the diameter of the bacteria, the most effective % reduction of the bacteria was observed from 2 um to 500 nm.

As the spacing between the pillars increased while keeping the diameter of the pillars constant as seen in Table 1-2, the % reduction of the bacteria increased.

With regard to Table 1-3, the diameter of the bacteria can be between 500 to 800 nm. For a 2 um groove, the bacteria will sit along the groove and thus be washed off whereas for a 500 nm groove, as this is similar to the diameter of the bacteria, the bacteria will be 'stuck' in the grooves. Hence, it is shown that for a pattern with a larger diameter than the size of the bacteria, a higher % bacterial reduction can be obtained.

With regard to Table 1-4, a U-groove pattern is more likely to trap bacteria than a V-groove as it is U-shaped. There is a higher tendency for a V-groove to trap a bacteria than a U-groove. Bacteria will thus lie in the 2 um U-groove and can be washed off leading to 60.45% reduction, whereas the 500 nm groove, due to its U shape, has a higher tendency to trap the bacteria, leading to a 33.14% reduction.

Table 2: Table Showing the % Reduction of *S. epidermidis* ATCC 12228 for Pillars with Different Dimensions and U Grooves

TABLE 2-1

Figure 4A:
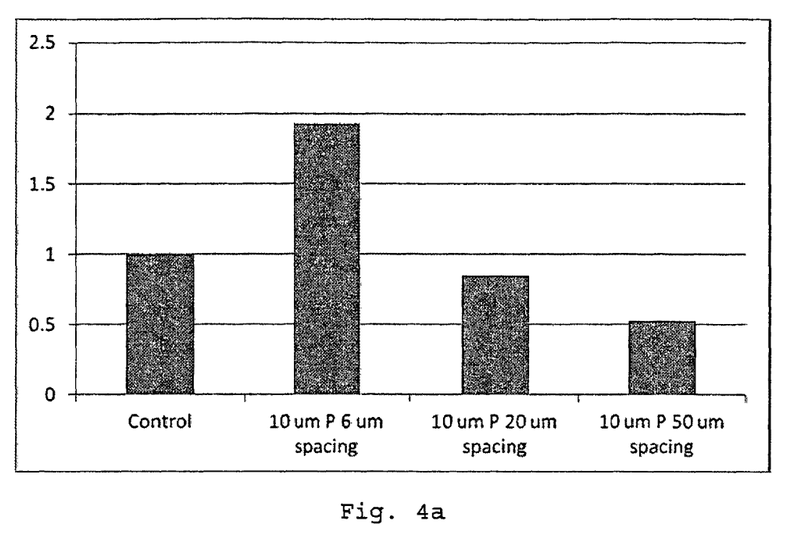
FIG. 4a is a bar graph showing the reduced mean number of adhered *S. epidermidis* ATCC 12228 per mm$^2$ for pillars with varying spacings.

(see also FIG. 4a)

| Patterns | % reduction |
| --- | --- |
| 10 um diameter with 20 um spacing | 15.09 |
| 10 um diameter with 50 um spacing | 47.00 |

TABLE 2-2

Figure 4B:
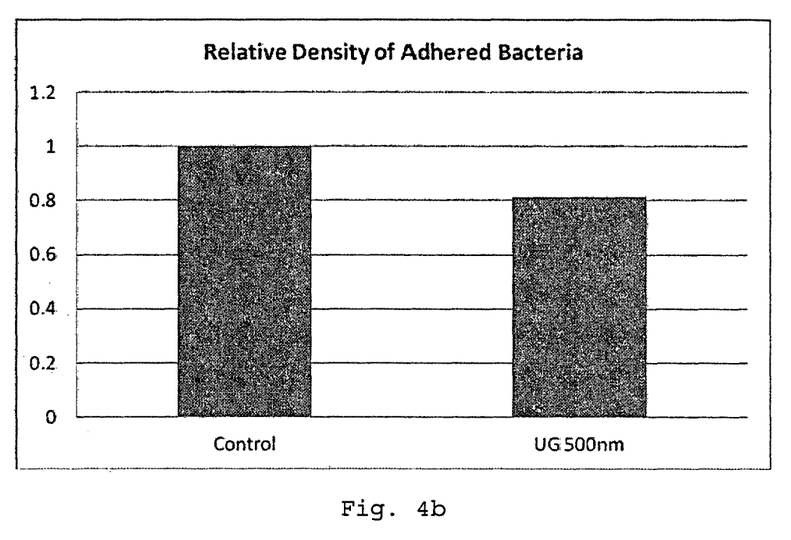
FIG. 4b is a bar graph showing the reduced mean number of adhered *S. epidermidis* ATCC 12228 per mm$^2$ for a U groove.

(see also FIG. 4b)

| Patterns | % reduction |
| --- | --- |
| U grooves 500 nm | 18.24 |

As shown in Table 2, as the spacing between the pillars increase, there is also a corresponding increase in the % reduction of the bacteria.

Table 3: Table Showing the % Reduction of *P. Tunicata* D2 for Pillars with Varying Pitch, V Grooves, U Grooves and Diamond Shapes

TABLE 3-1

Figure 5A:
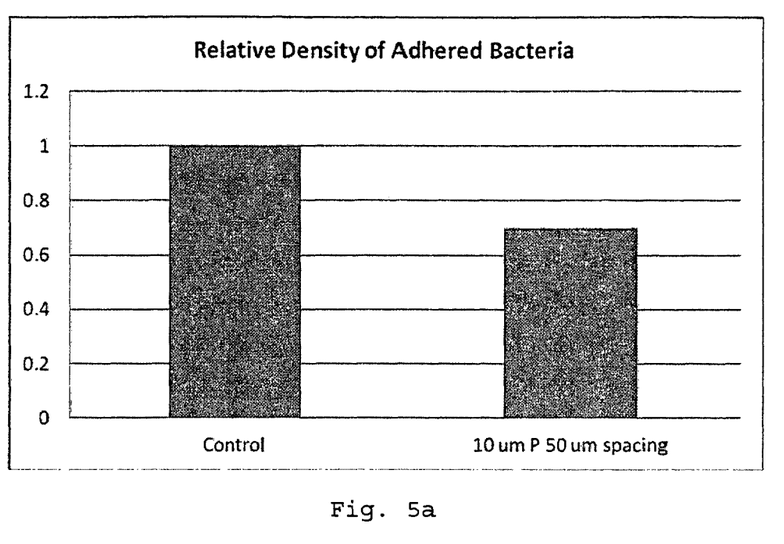
FIG. 5a is a bar graph showing the reduced mean number of adhered *P. Tunicata* D2 per mm$^2$ for pillars with varying spacings.

(see also FIG. 5a)

| Patterns | % reduction |
| --- | --- |
| 10 um diameter with 50 um pitch | 29.99 |

TABLE 3-2

Figure 5B:
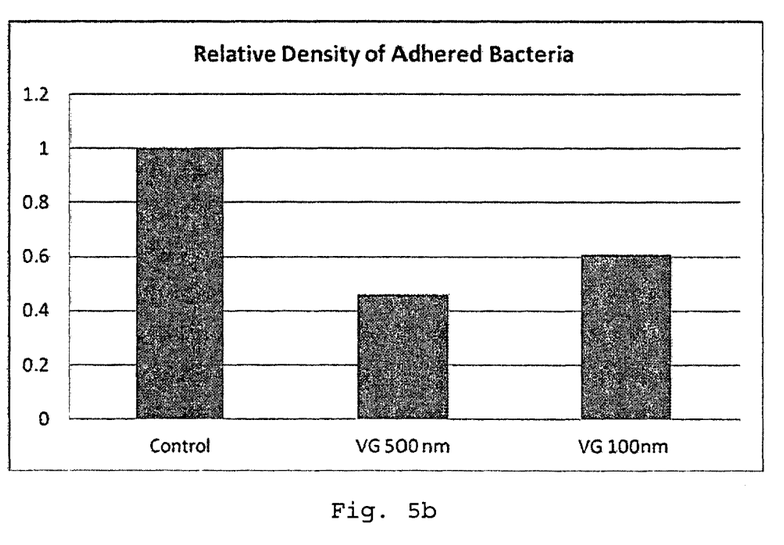
FIG. 5b is a bar graph showing the reduced mean number of adhered *P. Tunicata* D2 per mm$^2$ for V grooves of varying widths.
Figure 5C:
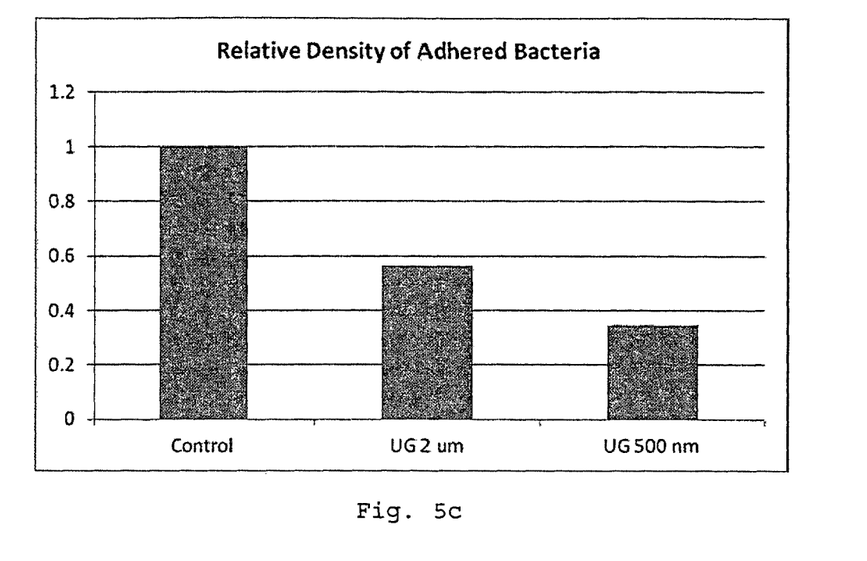
FIG. 5c is a bar graph showing the reduced mean number of adhered P. Tunicata D2 per mm² for U grooves of varying widths.

(see also FIG. 5b and FIG. 5c)

| Patterns | % reduction |
| --- | --- |
| V grooves 500 nm | 54.08 |
| V grooves 100 nm | 39.26 |
| U grooves 2 um | 43.56 |
| U grooves 500 nm | 65.42 |

As observed in the above tables, it can be seen that as the spacing increases, the % reduction of *E. coli* ATCC 25922 and *S. epidermidis* ATCC 12228 improve. However, as *P. Tunicata* D2 is a marine bacteria, its behavior may be different to the first two bacteria. In this regard, grooves (such as V-grooves and U-grooves) may be used for *P. Tunicata* D2.

Example 2

Figure 6:
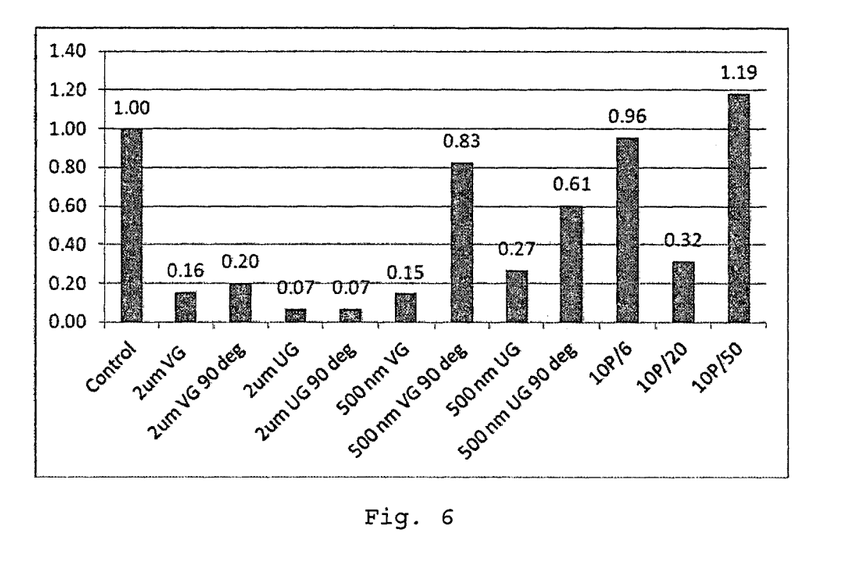
FIG. 6 is a bar graph showing the relative number of adhered microorganism on the test patterned substrates after the dip test.

The protocol 120 of FIG. 2 was used to test the effect of repeated dipping and rinsing steps on the attachment of the microorganism to the test patterned substrates 12. Firstly, a shake culture 10 of a test microorganism such as *E. coli* ATCC 25922 was cultivated for a period of time in sterile culture medium until the mid-log phase. The test patterned substrates (or imprints) 12 are loaded into 6-well plate and incubated with the shake culture 10 (containing ~1-2×10$^8$ CFU/ml of bacteria) for 1 hour at a temperature of 35° C. The test patterned substrates 12 having various nano and micron sized structures used in this example were chosen based on their effective reduction in bacterial attachment based on Example 1. After incubation, the test patterned substrate 12 was then loaded onto a dipper 20 such as a robot dipper and subjected to a series of controlled rinsing and dipping steps (according to the arrow 14) whereby the direction of the test patterned substrate 12 was controlled. The dipping conditions were as follows. The first and second rinsing step were done using a speed of 20 mm per second, the test patterned substrates 12 were immersed in sterile phosphate buffer (22a,22b) for 2 seconds and then retrieved at the same speed. The third rinsing step was done in sterile de-ionized water (24) at the same conditions. After 3 rounds of rinsing, the retained bacteria on the surface of the test patterned substrate 12 were mounted on a slide 16 and the concentration of bacteria was then determined by averaging the cell counts of five fluorescent images using the software Cell Profiler 18. The results of this dipping/rinsing example is shown in FIG. 6. In FIG. 6, for samples which has "90 deg" as part of its name, this means that the patterned area was tilted 90° from the normal. "VG" refers to V-grooves; "UG" refers to U-grooves; and "10P/x" refers to 10 um diameter with a spacing of x where x is 6 um, 20 um or 50 um.

From FIG. 6, it can be shown that most of the patterned substrates show a significant reduction in bacterial attachment, which is in agreement with the results in Example 1. It is to be noted that the data present in FIG. 6 and that from Example 1 are quantified by different methods. The data from FIG. 6 was done by controlled conditions and washing speeds were controlled with a dip coater, the samples were also washed three times in total whereas data from Example 1 were carried out by initial bacterial adhesion testing. The most prominent reduction were seen on the 2 um V and U groove structures. However, in both structures, the anticipated directional effects are absent. This can be due to 1) the low amount of adhered bacteria on these surfaces such that the washing did not have a significant effect; and 2) since the size of these groove are larger than the diameter of the rod-shape *E. Coli*, the bacteria that are already attached (albeit a small quantity) 'fit' tighyly into the groove.

The directional effect is pronounced in the group of groove structures with 500 nm dimension. Here, the size of the groove is smaller such that the bacteria are unable to 'fit' well into the groove. Hence, a substantial amount of bacteria are loosely present on the surface. As a result, the washing condition significantly affects the amount of bacteria remaining on the surface.

APPLICATIONS

The disclosed polymeric film having a surface with an array of patterned structures can be used in industries in which contamination with a biological material is to be reduced. Such industries can include medical (for example, medical implants, medical devices), food manufacturing (for example, food packaging, food manufacturing equipments and tools, drinking water containers or storage facilities), marine (such as marine infrastructure and seafaring vessels), water filtration industries (such as water purification systems) and construction (such as on building material surfaces, optical windows).

The reduction in the biological material attachment may not require the use of chemical treatment of the surface or the adhesion of a coating on the surface. Hence, the problems of chemical contamination, environmental or health toxicity and lack of long-term durability that are commonly associated with such chemical methods are not present in the disclosed structured polymeric films. In addition, since chemical treatment is not necessary, the disclosed polymeric films can be used in a number of diverse applications that would not be otherwise possible with the conventional chemical treatments because of chemical interactions or inhibition with the targeted application.

The disclosed polymeric films need not be sterilized in order to reduce the attachment of the biological material. Hence, there is no need to continuously sterilize the polymeric film to ensure minimal contamination of the biological material when the polymeric film is exposed to a non-sterile environment.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A polymeric film, comprising:
    a surface,
    wherein the surface of the polymeric film comprises an array of patterned structures,
    wherein topographies of the array of patterned structures are selected and arranged so that when the surface of the polymeric film is rinsed and/or dipped in a fluid, the array of patterned structures induces a turbulent fluid flow and removes biological material thereon, and
    wherein when a predetermined space or a predetermined width of the topographies of the polymeric film is larger than a diameter or dimension of the biological material, the rinsed and/or dipped surface of the polymeric film is characterized such that it exhibits a reduced attachment of the biological material.

2. The polymeric film according to claim 1, wherein said array of patterned structures comprises of pillars or grooves.

3. The polymeric film according to claim 2, wherein said pillars are micron-sized or nano-sized.

4. The polymeric film according to claim 2, wherein said pillars have diameters that are individually selected from the range of 10 μm to 50 μm.

5. The polymeric film according to claim 4, wherein said pillars have diameters that are individually selected from the group consisting of 25 nm, 100 nm, 500 um, 2 μm and 10 μm.

6. The polymeric film according to claim 2, wherein the spacing between a pair of pillars is the same as the spacing between another pair of pillars.

7. The polymeric film according to claim 2, wherein the spacing between a pair of pillars is different from the spacing between another pair of pillars.

8. The polymeric film according to claim 2, wherein said spacing is larger than the size of said biological material.

9. The polymeric film according to claim 1, wherein said spacing is selected from the range of 10 nm to 100 μm or from 10 μm to 100 μm.

10. The polymeric film according to claim 2, wherein said spacing is in the nano-scale.

11. The polymeric film according to claim 2, wherein said pillars have a diameter of 10 μm and a spacing in the range of 6 μm to 50 μm.

12. The polymeric film according to claim 2, wherein said pillars have diameters individually selected from the range of 25 nm to 10 μm and spacings that are equal to the diameters of said pillars.

13. The polymeric film according to claim 2, wherein said grooves have an anisotropic cross-sectional shape.

14. The polymeric film according to claim 2, wherein grooves have a width in the range of 100 nm to 5 m.

15. The polymeric film according to claim 2, wherein said grooves have a V-shaped cross section.

16. The polymeric film according to claim 15, wherein said V-shaped groves have a width selected from 100 nm, 500 nm or 2 μm, wherein said width is measured from the top of said groove.

17. The polymeric film according to claim 2, wherein said grooves have a U-shaped cross section.

18. The polymeric film according to claim 17, wherein said U-shaped groves have a width selected from 500 nm or 2 μm, wherein said width is measured from the top of said groove.

19. The polymeric film according to claim 1, wherein said biological material is selected from the group consisting of proteins, eukaryotic organisms, bacteria, viruses and fungi.

20. The polymeric film according to claim 19, wherein said bacteria is selected from the group consisting of gram negative bacteria, gram positive bacteria and marine bacteria.

21. The polymeric film according to claim 20, wherein said bacteria is selected from the group consisting of *E. coli* ATCC 25922, *S. epidermidis* ATCC 12228 and *P. Tunicata* D2.

* * * * *